United States Patent
Stoner et al.

Patent Number: 5,252,322
Date of Patent: Oct. 12, 1993

[54] SKIN TANNING COMPOSITIONS CONTAINING IMIDAZOLES

[75] Inventors: Karla L. Stoner, Frederick, Md.; Leon M. Wilkins, North Andover, Mass.

[73] Assignee: The Gillette Company, Boston, Mass.

[21] Appl. No.: 815,867

[22] Filed: Jan. 3, 1992

Related U.S. Application Data

[63] Continuation of Ser. No. 667,379, Mar. 12, 1991, abandoned, which is a continuation of Ser. No. 410,898, Sep. 22, 1989, abandoned.

[51] Int. Cl.⁵ .................. A61K 7/40; A61K 7/42; A61K 7/44; A61K 7/48
[52] U.S. Cl. ..................... 424/59; 424/47; 424/60; 424/63; 514/844; 514/847; 514/944
[58] Field of Search .................. 424/59, 60, 63

[56] References Cited

U.S. PATENT DOCUMENTS

| | | | |
|---|---|---|---|
| 2,104,492 | 1/1938 | Merkel et al. | 424/59 |
| 2,334,348 | 11/1943 | Miglarese | 424/59 |
| 3,020,276 | 2/1962 | Hughes et al. | 424/65 X |
| 4,447,431 | 5/1984 | Sallmann | 424/60 |

FOREIGN PATENT DOCUMENTS

| | | | |
|---|---|---|---|
| 3515402 | 10/1986 | Fed. Rep. of Germany | 424/63 |
| 45-39639 | 12/1970 | Japan | 424/59 |
| 0164504 | 9/1983 | Japan | 424/59 |

OTHER PUBLICATIONS

Pieper et al, Chem. Abs., 1986, vol. 106(10) 69095j (Abstract of Germany Offen 3, 515, 402 above).

*Primary Examiner*—Dale R. Ore
*Attorney, Agent, or Firm*—Burns, Doane, Swecker & Mathis

[57] ABSTRACT

A skin tanning composition comprising an effective amount of imidazole or an imidazole derivative in a dermatologically acceptable vehicle.

10 Claims, No Drawings

SKIN TANNING COMPOSITIONS CONTAINING IMIDAZOLES

This application is a continuation, of application Ser. No. 667,379, filed Mar. 12, 1991 which is a continuation of application Ser. No. 410,898 filed Sep. 22, 1989 both now abandoned.

BACKGROUND OF THE INVENTION

The present invention relates to skin tanning compositions, and more specifically, compositions which induce tanning of the skin without the skin having been subjected to ultraviolet radiation.

The look of a "healthy" tan is highly desirable amongst certain segments of the world's population and is therefore a commercially important consideration. Developing and maintaining a natural tan is a time consuming process with potentially harmful short and long term side effects. These side effects range from mild sunburn to premature skin aging and, most seriously, to various forms of skin cancer.

Because of these dangers inherent in long term exposure to the sun, and the time and effort involved in acquiring such a tan, considerable research has been conducted for methods which would produce a 'sunless" tan. While several options are currently available, none are completely satisfactory. Tanning salons produce essentially the same skin damage as exposure to the sun because they employ ultraviolet light in much the same manner as solar radiation. Commercially available tanning compositions merely color the skin, are often difficult to apply, and the result obtained varies considerably depending upon the user's skin color prior to application.

In view of these and other problems, the search has continued for compositions which induce tanning of the skin without a need for exposure to ultraviolet radiation.

SUMMARY OF THE INVENTION

The present invention is a skin tanning composition comprising an effective amount of a compound of the formula:

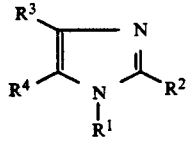

wherein
$R^1$ through $R^4$ can be the same or different and are hydrogen; phenyl; $C_1$-$C_6$ alkyl unsubstituted or substituted by phenyl, hydroxyl, carboxy, benzyloxy, amino, halogen, carboxylic acid, sulfonate or phosphate or —$CH_2$—$CH(COOR')NR''R'''$ where R', R", and R''' are the same or different and are hydrogen or $C_1$-$C_4$ alkyl; in a dermatologically acceptable vehicle.

DETAILED DESCRIPTION OF THE INVENTION

The present invention is a skin tanning composition comprising an effective amount of a compound of the formula:

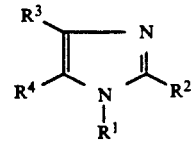

wherein
$R^1$ through $R^4$ can be the same or different and are hydrogen; phenyl; $C_1$-$C_6$ alkyl unsubstituted or substituted by phenyl, hydroxyl, carboxy, benzyloxy, amino, halogen, carboxylic acid, sulfonate or phosphate or —$CH_2$—$CH(COOR')NR''R'''$ where R', R", and R''' are the same or different and are hydrogen or $C_1$-$C_4$ alkyl; in a dermatologically acceptable vehicle.

Preferred compounds within the above group are those in which: (a) $R^1$ is hydrogen; (b) $R^2$ is hydrogen; an oxy group; or $C_1$-$C_6$ alkyl unsubstituted or substituted by a hydroxy, carboxy, carboxylic acid, or aldehyde group; (c) $R_3$ is hydrogen or —$CH_2$—$CH(COOR')NR''R'''$ where R', R", and R''' are the same or different and are hydrogen or $C_1$-$C_4$ alkyl; and (d) $R^4$ is hydrogen, or $C_1$-$C_6$ alkyl unsubstituted or substituted with a hydroxy or carboxylic acid group.

The most preferred compound within the above group of compounds is imidazole. However, other compounds give desirable results provided that appropriate concentrations are employed and the pH is controlled within a suitable range.

While not wishing to be bound by theory, it is believed that the present compounds function by stimulating the natural processes in the skin which result in a tan. It is believed that this is why a tan resulting from the use of the compounds of the present invention is indistinguishable from a tan produced by exposure to the sun. Since the compounds are believed to function by acting upon processes within the cells, it is important that the vehicle employed be such that effective skin penetration is obtained. Since certain of the compounds have a limited solubility in aqueous or alcoholic solutions, it may be necessary to employ other vehicles to provide an effective concentration. Typically a concentration of at least 0.5M is necessary to provide a suitable tan. The preferred range of concentrations is from 0.5M to 1.0M. Concentrations above 2.0M are less preferred because skin irritation may result and no additional tanning benefit would be expected.

SCREENING

A screening test is employed to select compounds in vitro before in vivo testing. The better compounds are found to stimulate higher levels of tyrosinase activity in cell cultures. Often the increase in tyrosinase activity is accompanied by a small decrease in cell number.

To obtain more rapid results, the tests can be run with a melanoma cell line such as Cloudman S91 melanoma cells. However, if desired, normal human melanocytes (NHM) can also be employed. The compounds to be tested are added as aqueous solutions to the cell culture medium. After four days, the cells are harvested and counted, and a tyrosinase activity assay and a total protein determination are run on cell pellets.

Dose-response curves from tyrosinase assays of cells stimulated with imidazole have slopes of about 1.1.

| DPM/1000 cells | |
| --- | --- |
| Concentration (mM) | DPM |
| 0 | 111.9 |
| 0.5 | 210.7 |
| 1.0 | 263.2 |
| 5.0 | 329.2 |
| 10.0 | 516.1 |

Various derivatives of imidazole were tested in the same manner with the following results:

4-(hydroxymethyl)imidazole

Tests employing the S91 cell line at concentrations of 0 (control), 0.1, 0.25, and 0.5 mM found tyrosinase activity slightly increased at 0.25 and 0.5 mM.

4-imidazoleacetic acid

Testing on the S91 cell line at concentrations of 0 (control), 0.5, and 10 mM revealed a dose dependent decrease in tyrosinase activity. However, this may have been due to the acidic pH of the test solutions.

2-imidazolidone

Testing in NHM at concentrations of 0 (control), 0.5, 10, and 50 mM resulted in moderate inhibition of tyrosinase activity. However, in the S91 cell line testing of the same concentrations resulted in a slight increase in tyrosinase activity at 50 mM.

2-imidazolecarboxaldehyde

Testing in the S91 cell line at concentrations of 0 (control), 0.1, 0.25, and 0.5 mM showed decreased activity at 0.1 and 0.25 mM. However, tyrosinase activity was elevated at 0.5 mM.

L-histidine monochloride monohydrate

Testing in the S91 cell line at concentrations of 0 (control), 0.5, and 10 mM showed increased tyrosinase activity at 0.5 mM.

IN VIVO TESTING

To confirm the results of in vitro testing, in vivo testing was conducted on pigmented guinea pig skin. Five animals were used in each of the treatment or control groups.

Procedure

1. Animals were clipped in a suitably pigmented area over the back or flank and chemically depilated prior to the first treatments. The area was at least 4 cm$^2$. The treatment site was 3 cm$^2$ and was carefully marked. Photographs of areas to be treated were taken prior to initial treatments. Animals were clipped as needed throughout the study, depilation was only done prior to evaluations.
2. Concentrations of imidazole of 0.1, 0.5, 1.0 and 2.0M were applied as a liquid in 50% EtOH. 100 μL volumes were applied via pipette and glass rod with minimal rubbing of the skin.
3. Treatments were made daily, 5 days per week for 3 weeks. Visual observations and photographic records were made at the study midpoint and 24 hours after the last treatment. Animals were clipped and depilated prior to these evaluations.
4. The animals were monitored for two weeks following the last treatment. At the end of the fifth week, animals were photographed.

Visual observations of the treated sites showed darkening for all areas, with the most tanning occurring at 0.5 to 1.0M. The 2.0M solution appeared to mildly irritate the skin of some of the animals.

Darkening was observed after 5-10 treatments and continued to increase through the third week.

In order to further illustrate the present invention and the advantages thereof, the following specific examples are given, it being understood that these examples are intended only to be illustrative without serving as a limitation on the scope of the present invention.

EXAMPLES

EXAMPLE 1—AEROSOL QUICK BREAKING FOAM

| | percent |
| --- | --- |
| Myristic acid | 1.3 |
| Stearic acid | 5.0 |
| Cetyl alcohol | 0.5 |
| Isopropyl myristate | 1.3 |
| Glycerin USP | 5.0 |
| Sunscreen agent | 1.0 |
| L-43 Silicone fluid | 1.0 |
| Triethanolamine | 3.0 |
| Distilled Water | 67.0 |
| Benzyl alcohol | 1.0 |
| Perfume oil | 0.3 |
| Imidazole | 13.6 |
| | 100.0 |

Procedure

Add distilled water and triethanolamine and heat to 70° C. Then add stearic acid to form triethanolamine-stearic acid salt which is the emulsifier. Add glycerin, followed by myristic acid, cetyl alcohol, isopropyl myristate, the sunscreen agent and L-43 silicone fluid, keeping the temperature at 70° C. Then cool with mixing and add benzyl alcohol and imidazole as the formulation approaches 30°-40° C. Add perfume and package.

EXAMPLE 2—MOISTURIZING BODY LOTION

| | percent |
| --- | --- |
| A. | |
| Stearic Acid | 2.2 |
| Glycol Stearate | 0.4 |
| Glyceryl Stearate | 0.6 |
| Lanolin Oil | 1.0 |
| Emulsifying Wax NF | 1.0 |
| Sorbitan Stearate | 1.5 |
| Liquid Absorption Base | 5.0 |
| Myristyl Myristate | 1.8 |
| Propyl paraben | 0.1 |
| B. | |
| Propylene glycol | 5.0 |
| Glycerin | 2.0 |
| Magnesium Aluminum Silicate | 0.1 |
| Triethanolamine | 1.0 |
| Emeressence 1160 Phenoxyethanol | 0.7 |
| Methyl paraben | 0.2 |
| Deionized water | 70.6 |
| C. | |
| Imidazole | 6.8 |
| | 100.0 |

Procedure

Disperse magnesium aluminum silicate in water. Heat (A) and (B) separately to 78° C. Add (B) to (A) with stirring. Cool, add (C), with stirring, perfume and color. Pour into containers.

EXAMPLE 3—EMOLLIENT SUNSCREEN CREAM

| | percent |
|---|---|
| A. | |
| (Octyl Dimethyl PABA) | 3.0 |
| Lanolin Acids | 3.0 |
| Stearic Acid | 2.0 |
| Glyceryl Stearate | 9.0 |
| Isopropyl Myristate | 3.0 |
| Acetate Ester | 1.5 |
| Phenyl Dimethicone | 1.0 |
| PEG-40 Sorbitan Diisostearate | 0.5 |
| Propyl paraben | 0.1 |
| B. | |
| Glycerin | 2.5 |
| Triethanolamine | 1.0 |
| Methyl paraben | 0.2 |
| Deionized water | 66.4 |
| C. | |
| Imidazole | 6.8 |
| | 100.0 |

This formulation includes a sunscreen to provide additional protection against UV damage.

Procedure

Heat (A) to 80° C. and (B) to 82° C. Add (A) to (B) slowly with stirring. Cool with stirring to 50° C. Add perfume and (C), and cool with stirring to 38° C.

EXAMPLE 4—MOISTURIZING HAND AND FACE CREAM

| | percent |
|---|---|
| A. | |
| Stearic Acid | 3.5 |
| Acetylated Lanolin | 4.0 |
| Propylene Glycol Stearate | 2.5 |
| Propyl paraben | 0.1 |
| B. | |
| Propylene glycol | 3.5 |
| Triethanolamine | 0.7 |
| Emeressence 1160 Phenoxyethanol | 0.7 |
| Methyl paraben | 0.2 |
| Deionized water | 78.0 |
| C. | |
| Imidazole | 6.8 |
| | 100.0 |

Procedure

Heat (A) and (B) separately to 75° C. With stirring, add (B) to (A). Add (C) with stirring when temperature falls below 50° C. Continue stirring to room temperature.

EXAMPLE 5—CLEAR EMOLLIENT GEL

| | percent |
|---|---|
| Emulsufying Acetate Ester | 5.00 |
| Polysorbate 20 | 2.00 |
| SD Alcohol 40 | 47.46 |
| Carbopol 941 (2½% aq.) | 36.60 |

| -continued | |
|---|---|
| | percent |
| Benzophenone-4 | 0.03 |
| Sequestrene Na2 (Disodium EDTA) | 0.01 |
| Diisopropanolamine (10% aq.) | 1.80 |
| Perfume | 0.30 |
| Imidazole | 6.80 |
| | 100.00 |

Procedure

Dissolve imidazole in SD alcohol 40 and then add all ingredients in order with high speed agitation until clear.

Although the present invention has been described in terms of various preferred embodiments, one skilled in the art will recognize that various modifications, substitutions, omissions, and changes may be made without departing from the spirit thereof. Accordingly, it is intended that the scope of the present invention be limited only by the scope of the following claims.

What is claimed is:

1. A method of tanning the skin in the absence of exposure to ultraviolet radiation comprising application to the skin of a skin tanning effective amount of a compound of the formula:

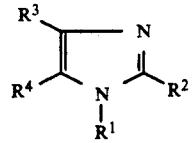

wherein $R^1$ through $R^4$ can be the same or different and are hydrogen; phenyl; $C_1$-$C_6$ alkyl unsubstituted or substituted by phenyl, hydroxy, benzyloxy, amino, halogen, carboxylic acid, sulfonate or phosphate; or $CH_2$—$CH(COOR')$ $NR''R'''$ where $R'$, $R''$, and $R'''$ are the same or different and are hydrogen or $C_1$-$C_4$ alkyl; in a dermatologically acceptable vehicle.

2. The method of claim 1 wherein $R^1$ is hydrogen.

3. The method of claim 1 wherein $R^2$ is hydrogen; an oxy group; or $C_1$-$C_6$ alkyl unsubstituted or substituted by a hydroxy, carboxylic acid, or aldehyde group.

4. The method of claim 1 wherein $R^3$ is hydrogen or —$CH_2$—$CH(COOR')NR''R'''$ where $R'$, $R''$, and $R'''$ are the same or different and are hydrogen or $C_1$-$C_4$ alkyl.

5. The method of claim 1 wherein $R^4$ is hydrogen, or $C_1$-$C_6$ alkyl unsubstituted or substituted with a hydroxy or carboxylic acid group.

6. The method of claim 1 wherein $R^1$ is hydrogen; $R^2$ is hydrogen, an oxy group, or $C_1$-$C_6$ alkyl unsubstituted or substituted by a hydroxy, carboxylic acid, or aldehyde group; $R^3$ is hydrogen or —$CH_2$—$CH(COOR')NR''R'''$ where $R'$, $R''$, and $R'''$ are the same or different and are hydrogen or $C_1$-$C_4$ alkyl; and $R^4$ is hydrogen or $C_1$-$C_6$ alkyl unsubstituted or substituted with a hydroxy or carboxylic acid group.

7. The method of claim 1 wherein the compound is 4-(hydroxymethyl)imidazole; 4-imidazoleacetic acid, 2-imidazolidone, 2-imidazolecarboxaldehyde, or L-histidine monochloride monohydrate.

8. The method of claim 1 wherein the compound is imidazole.

9. The method of claim 1 wherein the compound is present at a concentration of at least 0.5M.

10. The method of claim 1 wherein the compound is present at a concentration of from 0.5M to 1.0M.

* * * * *

UNITED STATES PATENT AND TRADEMARK OFFICE
CERTIFICATE OF CORRECTION

PATENT NO. : 5,252,322
DATED : October 12, 1993
INVENTOR(S) : Karla L. STONER and Leon M. WILKINS It is certified that error appears in the above-indentified patent and that said Letters Patent is hereby corrected as shown below:

Column 1, line 27, after "produce a", delete "'" and insert --"--;
         line 59, after "phosphate", insert --;--.

Column 2, line 13, after "phosphate", insert --;--;
         line 21, after "(c)", delete "R3" and insert --$R^3$--.

Signed and Sealed this

First Day of February, 1994

Attest:

BRUCE LEHMAN

*Attesting Officer*      *Commissioner of Patents and Trademarks*